United States Patent [19]

Mao

[11] Patent Number: 5,780,689

[45] Date of Patent: Jul. 14, 1998

[54] SUPERACIDIC CATALYSTS FOR THE SYNTHESIS OF METHYL-TERT-BUTYL ETHER (MTBE)

[75] Inventor: Raymond Le Van Mao, Saint-Laurent, Canada

[73] Assignee: Societe Quebecoise D'Initiatives Petrolieres, Quebec, Canada

[21] Appl. No.: 520,821

[22] Filed: Aug. 30, 1995

Related U.S. Application Data

[62] Division of Ser. No. 728,157, Jul. 10, 1991, abandoned.

[51] Int. Cl.[6] ................................................. C07C 41/00
[52] U.S. Cl. ................................................. 568/698
[58] Field of Search ................................................. 568/698

[56] References Cited

U.S. PATENT DOCUMENTS

| | | | |
|---|---|---|---|
| 4,615,995 | 10/1986 | Le Van Mao | 502/64 |
| 4,847,223 | 7/1989 | Le Van Mao et al. | 502/62 |
| 4,873,392 | 10/1989 | Le Van Mao | 585/640 |
| 5,081,318 | 1/1992 | Knifton | 568/698 |
| 5,179,052 | 1/1993 | Knifton | 502/62 |
| 5,313,006 | 5/1994 | Knifton | 568/698 |

OTHER PUBLICATIONS

R. Le Van Mao et al., "Synthesis of Methyl Tertbutyl Ether (MTBE) Over Triflic Acid Loaded ZSM-5 and Y Zeolites", Catalysis Letters 6:321–330 (1990).

*Primary Examiner*—William R.A. Jarvis
*Assistant Examiner*—Dwayne C. Jones
*Attorney, Agent, or Firm*—Merchant, Gould, Smith, Edell, Welter & Schmidt

[57] ABSTRACT

In accordance with the present invention, there is now provided a novel selective catalyst useful for the synthesis of methyl-tert-butyl ether (MTBE) or ethyl-tert-butyl ether (ETBE) prepared by reacting isobutene with methanol or ethanol, respectively. More specifically, the catalyst of the present invention comprises from about 0.5 to about 7% by weight of triflic acid (trifluoro-methanesulfonic acid, $CF_3SO_3H$, hereafter referred to as TFA) incorporated onto an acid form Y zeolite.

17 Claims, 5 Drawing Sheets

FIG. 1

TGA (a) and DTA (b) of the H-Y/tfa (3) in air atmosphere (heating rate: 5 °C/mn).

FIG. 2

MTBE yields versus the reaction temperature, obtained with the Amberlyst 15 (●——●) the H-ZSM-5 (○——○) and the H-Y (□——□) catalysts, respectively.

FIG. 3

MTBE yields versus the reaction temperature, obtained with the H-ZSM-5/TFA (3) (o—o) and the H-ZSM-5/TFA (4) (□—□).

FIG. 4

MBTE yields versus the reaction temperature, obtained with the H-Y/TFA (3)

FIG. 5

C8 by-products yields versus the reaction temperature, obtained with the Amberlyst 15 (●——●), the H-Y (□——□), the H-Y/TFA (3) (★——★) and the H-ZSM-5/TFA (3) (○——○), respectively.

FIG. 7

Synthesis of MTBE. Effects of contact time and temperature on the dimethyl ether (DME) yield

SUPERACIDIC CATALYSTS FOR THE SYNTHESIS OF METHYL-TERT-BUTYL ETHER (MTBE)

CROSS-REFERENCE TO RELATED APPLICATION

The present application is a divisional application of U.S. Ser. No. 07/728,157 filed Jul. 10, 1991 abandoned on Aug. 31, 1995. The specification and drawings of application Ser. No. 07/728,157 are incorporated herein by reference.

FIELD OF THE INVENTION

The present invention relates to a novel catalyst for the selective synthesis of methyl-tert-butyl ether (MTBE). More particularly, the present invention relates to the acid form of a Y-zeolite onto which triflic acid (trifluoromethane sulfonic acid, $CF_3SO_3H$) has been incorporated, and to a process using this catalyst in the production of MTBE.

BACKGROUND OF THE INVENTION

Synthetic Y-type zeolites are crystalline alumino-silicate zeolites having a tridimentional pore system. These zeolites are used in many industrial catalytic reactions such as catalytic cracking (Fluid Cracking Catalysis or FCC). Their peculiar catalytic properties are mainly due to their regular framework with a pore size of approximately 7.4 angstroms, and also to their strong acidic sites.

The shape selectivity of the Y-type zeolite is the catalytic expression of many factors such as:

(i) the sieving effect, i.e. the capability of the zeolite to allow or to prevent the access of the reactive molecules into its pore system. This selection process is based on the critical diameter of the reactive molecules by comparison with the width of the zeolite pore openings;

(ii) the reverse sieving effect, i.e. the capability of the zeolite to allow product molecules having a certain critical diameter to diffuse out of its pores. Thus, in the case of a product molecule having a diameter exceeding the pore size of the zeolite, this molecule will have to undergo additional cracking into smaller molecules before diffusing out of the zeolite; and (iii) the effect on the reaction intermediates, i.e. the capability of reaction loci to determine the length and geometry of reaction intermediate species.

In the FCC field, the active sites are usually of very acidic nature. Such acidic sites are generated by exchanging the sodium ions originally present in the as-synthesized zeolite for protons and/or other cations such as lanthanium. In any event, it is now also thought that the acidic character of the acid form of Y-zeolite originates from the Bronsted centres created by the tetrahedral aluminium sites, although some Lewis acid sites may be formed by activating the zeolite at high temperature.

Since lead antiknock additives in gasoline will be banned in most industrialized countries by the end of this decade, octane boosters for fuels such as light alcohols, methyl-tert-butyl ether (MTBE) and ethyl-tert-butyl ether (ETBE) have been increasingly used in gasoline blend. MTBE, particularly, is an excellent candidate for replacing tetraethyl lead in gasoline. When compared to aromatic hydrocarbons which can be used to upgrade gasoline, MTBE does not evolve any toxic products of incomplete combustion in engines. Furthermore, MTBE does not provoke any demixing problem when blended with gasoline, which is not the case with methanol, for instance. MTBE, which is characterized with specifications close to those of gasoline, does not require dramatic modifications in the engine technology. MTBE being an oxygenate having a fairly high octane number, accordingly favors the clean combustion of gasolines and other fuels.

MTBE is currently synthesized industrially from methanol and isobutene over acidic ion-exchange resin, mostly the Amberlyst 15™ which is actually a macroreticular cation-exchange resin supplied by Aldrich Co. Even though the performance of the Amberlyst catalyst is good, there are several drawbacks to its use as a commercial catalyst, such as thermal instability, acid leaching from the resin surface, and high methanol/isobutene ratio which requires recycling efforts in the industrial process. Also, the use of Amberlyst results in the production of significant amounts of $C_8$ hydrocarbons as by-products, which reduce the yield of MTBE.

The ZSM-5 zeolite developed by Mobil Oil avoids such inconveniences. However, this zeolite is not as acidic as the Amberlyst type resin. In U.S. Pat. No. 4,847,223 and U.S. Pat. No. 4,873,392, it has been shown that by coating the ZSM-5 type zeolite with trifluoromethanesulfonic acid (triflic acid or TFA), it is possible to enhance the surface acidity of the ZSM-5 type zeolites. Such catalysts which are stable to temperatures of up to 240°–250° C., show exceptional catalytic to hydrocarbons, in particular to isobutene.

Though the use of ZSM-5 type zeolite, when combined with TFA, reduces the amount of $C_8$ hydrocarbons as by-products when compared to Amberlyst, the use of ZSM-5 provides a significantly lower yield of MTBE.

Accordingly, there is a great need for a catalyst for the preparation of MTBE, which while providing a high yield of MTBE, would at the same time, reduce the undesired $C_8$ hydrocarbons as by-products to a minimum.

SUMMARY OF THE INVENTION

In accordance with the present invention, there is now provided a novel selective catalyst useful for the synthesis of methyl-tert-butyl ether (MTBE) or ethyl-tert-butyl ether (ETBE) prepared by reacting isobutene with methanol or ethanol, respectively. More specifically, the catalyst of the present invention comprises from about 0.5 to about 7% by weight of triflic acid (trifluoro-methanesulfonic acid, $CF_3SO_3H$, hereafter referred to as TFA) incorporated onto an acid form Y zeolite. The process for the production of the catalyst of the present invention is very similar to the one described in U.S. Pat. Nos. 4,847,223 and 4,873,392.

It is preferred that the concentration of TFA be from about 0.5 to about 7% by weight in the catalyst and more preferably from about 3 to about 5% by weight. It is also preferred that the triflic acid incorporation be carried out by a uniform impregnation of TFA onto the Y zeolite particles in the presence of organic solvent, such as acetone. The resulting solid is heated at 80°–150° C. and preferably at 120°–140° C., for a period of time ranging from 1 to 24 hours. In its commercial use, the catalyst of the present invention is preferably incorporated in an inert filler, such as bentonite.

Also within the scope of the present invention is a process for the synthesis of MTBE and ETBE in the liquid phase (200 psig) at a temperature ranging from about 80 to about 100° C., preferably from 85° to 90° C., said process an acid form Y zeolite having incorporated therein from about 0.5 to about 7% by weight of TFA, preferably from 3 to 5% by weight.

DETAILED DESCRIPTION AND PREFERRED EMBODIMENTS

The surprisingly high performance of the catalyst of the present invention in the synthesis of MTBE and ETBE is due to:

i) the cooperative action of the zeolite sites and the triflic acid layer which leads to higher acid density and strength. It has been found that triflic acid strongly reacts with the silica-alumina zeolite surface upon heating at 80°–150° C. The resulting complexed triflic acid is stable at temperatures of up to 240°–250° C., although pure TFA boils at 161° C. under atmospheric pressure;

ii) the larger pore size of the Y zeolite (7.4 Angstroms) when compared to that of the ZSM-5 zeolite (pore size—5.5 Angstroms), which allows a higher loading of triflic acid onto the proton richer Y zeolite surface without diffusion problems, mostly for the relatively bulky isobutene as co-reactant. Therefore, the 3 wt % TFA/Y zeolite is much more active than 3 wt % TFA/ZSM-5 zeolite. These are the optimum triflic acid loading for these two zeolites in terms of catalytic performance; and iii) the shape selectivity of the Y zeolite, which results in the production of the same amount of MTBE as the Amberlyst 15 but negligible amount of $C_8$ hydrocarbons as by-products. Even at 65° C., the Amberlyst 15 produces a significant amount of $C_8$ hydrocarbons as by-products, thus revealing a lack of shape selectivity due to the certain openness of the resin structure.

The TFA incorporated Y zeolite catalyst of the present invention possesses the combined catalytic properties of the two current commercially available catalysts, Amberlyst 15 and ZSM-5/TFA. It is at least as active as the Amberlyst-type resin, at a relatively low reaction temperature (85°–90° C.), and as selective as the ZSM-5 zeolite: the production of $C_8$ hydrocarbons as by-products is extremely low when compared to that of the Amberlyst resin at 65° C. and the catalyst is thermally and chemically very stable.

The H-Y zeolite used in the preparation of the catalyst of the invention has a pore size of at least 7.4 angstroms.

The basic system can be a pure Y zeolite in acid form (H-Y) or a composite Y zeolite-asbestos material, also called Y chrysozeolite. The latter composite material is prepared by a multi-step process which includes the partial leaching of the metallic components, such as magnesium and iron, from the zeolite chrysotile asbestos fibers, followed by the in situ zeolite crystallization, and ended by the incorporation of the acid sites into the zeolite lattices (see, for example, U.S. Pat. No. 4,511,667, Le Van Mao et al.). The acid form of the Y zeolite may be obtained by heating the LZY-82™ (Linde, a division of Union Carbide) in air at 550° C. for 10 hours.

The preferred catalyst of the present invention is prepared by intimately mixing a H-Y zeolite having a TFA content of from about 0.5 to about 7% by weight, with 5 to 50% by weight of an inert filler such as bentonite or colloidal silica, for example, LUDOX™, manufactured and sold by DuPont & Co. Preferably, 20% by weight of inert filler is used. The resulting mixture is made into a paste by adding a sufficient amount of distilled water. Although the amount of water incorporated may range from about 0.5 to about 3 ml per gram of solid used, 1 ml of water per gram of the solid is preferred. The resulting product is then dried in air at a temperature ranging from 120° C. to 150° C. for 1 to 24 hours. The resulting solid is then ready to be used as a catalyst for the synthesis of MTBE or ETBE.

SYNTHESIS OF MTBE AND ETBE

Although the commercial process for synthesizing MTBE is carried out at 60°–70° C. in liquid phase (pressure~200 psig), gas phase reaction at atmospheric pressure is currently used for the catalyst development, in order to easily assess the catalytic properties of the prepared samples.

For the catalytic testing, a vertically mounted stainless-steel fixed-bed reactor of 2.5 cm diameter and 30 cm in length was used. The reactor had a preheating and a reaction zone monitored by two chromel-alumel thermocouples in a thermocouple well positioned at the center of the reactor. The temperature controller was a potentiometric, time-proportioning controller, with temperature control achieved by adjusting power input to each zone. Gaseous isobutene was fed to the reactor, and its flow rate was monitored by using a gas transducer connected to a digital mass flowmeter and a gas volume totalizer. Liquid methanol was pumped, by means of a Milton Roy pump, from a graduated reservoir to the preheating zone of the reactor currently kept at about 100° C. to vaporize methanol. Condensable reaction products were collected in a flask maintained at −5° C. The gaseous products were analysed on-line with a Hewlett-Packard 5790 gas chromatograph equipped with a FID and a reporting integrator Model HP-3392. Separation of the gaseous phase was achieved on series-packed columns of 5 m of sequalane on Chromosorb P and 2.5 m of Carbopack (Supelco.), graphite coated with picric acid. Analysis of the liquid phase was done by using a 50 m PONA HP capiliary column and a FID using 2,2-dimethylibutane as external standard.

Results from the gas phase synthesis of MTBE were computed as follows. The two main by-products of the reaction were $C_8$ diisobutene (or 2,4,4-trimethyl-1-pentene) and its isomer 2,4,4-trimethyl-2-pentene. Trace amounts of trimers were also detected. The production of terbutanol was negligible. The yield of product(s) i was calculated as follows:

$$Y_i = (N_i/N_{iso}) \times 100 (C \text{ atom } \%)$$

wherein $N_i$ and $N_{iso}$ are the number of carbon atoms of product(s) i and of feed isobutene, respectively.

Finally, the molar ration R (methanol/isobutene) was determined as the ratio of number of moles of methanol to the number of moles of isobutene in the feed. The reaction parameters were as follows:

weight of catalyst=12 g;

flow rate of feed isobutene=0.06 to 0.08 C atom/h;

R=0.8 to 1.2;

temperature=55°–100° C. (+/−1° C).

For the study of the influence of the contact time on the MTBE (or ETBE) yield, R=1.5–2.0 and the flow rate of feed isobutene was varied from 0.06 to 1.07 mole/h. The contact time, expressed in hours, is defined as the reciprocal of the hourly weight space velocity (W.H.S.V.). The latter parameter is the ratio of the total weight (in g) of reactants (methanol or ethanol+isobutene) injected per hour, to the weight (in g) of catalyst used.

The Amberlyst 15 was purchased from Aldrich Co. and used without any further purification.

The following examples are provided to illustrate the present invention rather than limiting its scope.

EXAMPLE 1

H-Y zeolite catalyst

The acid form of the Y zeolite (H-Y) was obtained by heat activation of the LZY-82™ (ammonium form, from Linde) in air at 550° C. for 10 hours.

The final catalyst was prepared according to the following procedure: the powder acid form of the Y zeolite synthesized above, was mixed with bentonite (20 wt %) and made into a paste with distilled water. 1 ml of water was used for each gram of zeolite. Finally, the extrudates were dried at 120° C. for 12 hours. Table 1 reports some physico-chemical and adsorptive properties of H-Y zeolite, as well as for the catalysts prepared in Examples 2–4.

EXAMPLE 2

H-ZSM-5 zeolite catalyst

The ZSM-5 zeolite was synthesized in autoclave according to the known method of Argauer and Landolt (U.S. Pat. No. 3,702,886). The as-synthesized solid was washed with distilled water until the washing liquid had reached a pH lower than 9, dried at 120° C. for 12 hours, and activated at 550° C. in air for 12 hours. The acid form (H-ZSM-5) was prepared according to the method described in Example 1 of U.S. Pat. No. 4,847,223. The final catalyst was obtained according to the method described in Example 1.

EXAMPLE 3

H-Y/TFA catalyst

The H-Y zeolite (powder form) of Example 1 was treated with triflic acid according to the following procedure: 0.3 g of triflic acid (TFA, 98% from Fluka Chemie AG) were dissolved in 15 ml of pure acetone. This solution was then slowly added to 10 g of H-Y powder. The resulting suspension was allowed to stand and dried in the air at room temperature. The solid was washed quickly with 5 ml of acetone and then heated at 120°–140° C. in air for 12 hours, resulting in an H-Y/TFA zeolite having a TFA content of 3%. The final catalyst was obtained by using the method of preparation of extrudates as described in Example 1.

EXAMPLE 4

H-ZSM-5 zeolite catalyst

The triflic acid addition (3 or 4 wt %) onto the H-ZSM-5 zeolite powder was done according to the procedure of Example 3. 0.3 g and 0.4 g of triflic acid were used, respectively. The final catalyst extrudates were obtained by using the method of preparation as described in Example 1.

ANALYSIS OF THE RESULTS

As shown in Table 1, the TFA loading onto the H-Y and H-ZSM-5 zeolites did not lead to significant changes in the degree of crystallinity. However, the surface area and the water/n-hexane adsorption capacities of the resulting materials were significantly decreased. This might be attributed to some reduction in the zeolite pore size due to the presence of the TFA layer on the zeolite surface.

TABLE 1

Some physico-chemical and adsorptive properties of the zeolite catalysts

| Zeolite | Si/Al | TFA loading (wt %) | Degree of crystallinity (%) | Surface area (Langmuir $m^2/g$) | Adsorption (vol %) n-hexane | Adsorption (vol %) water |
|---|---|---|---|---|---|---|
| H-ZSM-5 | 18 | 0 | 100 | 360 | 14.3 | 10.6 |
| H-ZSM-5/TFA (3) | 18 | 3 | 99 | 209 | 9.1 | 10.9 |
| H-Y | 2.5 | 0 | 100 | 576 | 22.8 | 35.8 |
| H-Y/TFA(3) | 2.5 | 3 | 99 | 300 | 14.9 | 24.2 |

Figure 1:
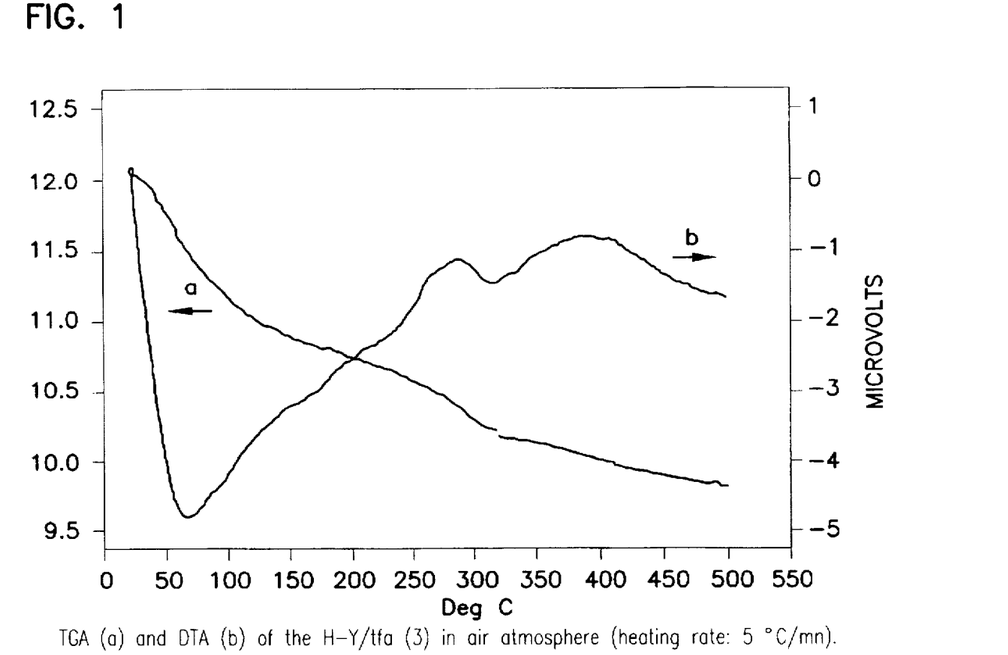
FIG. 1 illustrates the thermal analysis curves obtained with the H-Y/TFA (3%) sample.

The existence of the two exothermic peaks at temperatures higher than 240°–260° C., as illustrated in FIG. 1, indicates that the complexed TFA species decompose only at temperatures higher than those reported previously.

Figure 2:
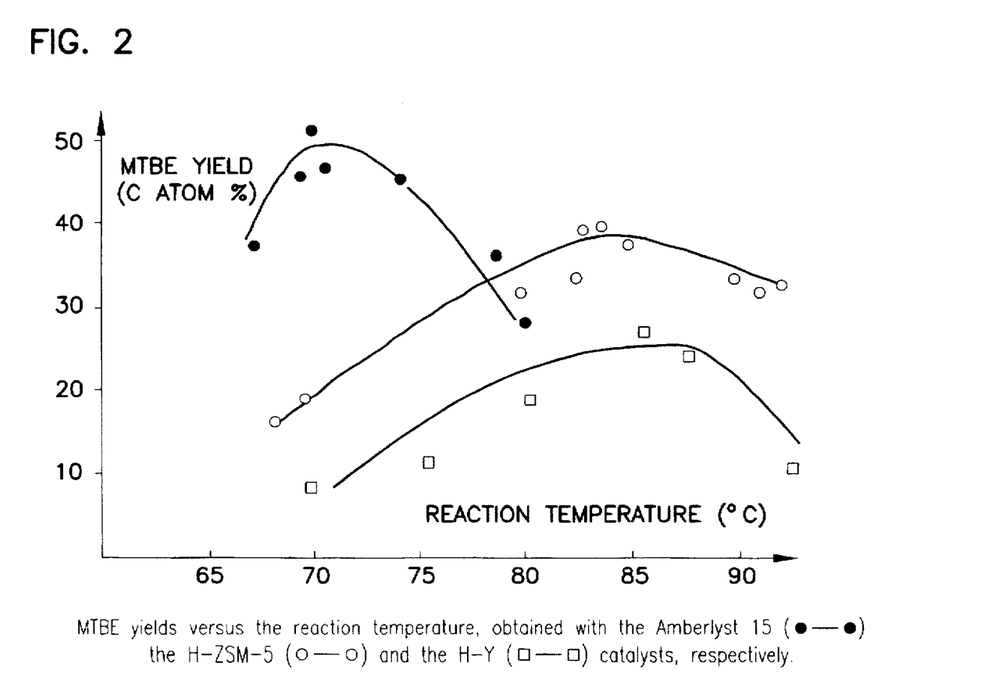
FIG. 2 illustrates the variation of the MTBE yield with the temperature observed with the commercial Amberlyst 15, the H-ZSM-5 zeolite and the H-Y zeolite, respectively.

Referring to Table 2, and FIG. 2, it can be seen that there is a clear sequence in the catalyst activity for production of MTBE as follows:

Amberlyst>>H-ZSM-5>H-Y

TABLE 2

Yield of MTBE versus reaction temperature (R = 1.0 and contact time = 2.5 h). (Maximum) are the maximum MTBE yields as derived from curves of FIG. 2.

| CATALYST | TEMPERATURE (°C.) | MTBE YIELD (C atom %) |
|---|---|---|
| Amberlyst 15 | 67 | 38.1 |
|  | 69 | 46.9 |
|  | 70 | 51.8 |
|  | 71 | 48.1 |
|  | 74 | 46.2 |
|  | 78 | 36.8 |
|  | 80 | 28.6 |
| (Maximum) | 70 | 48.8 |
| H-ZSM-5 | 68 | 16.2 |
|  | 70 | 19.4 |
|  | 80 | 32.5 |
|  | 82 | 34.4 |
|  | 83 | 40.0 |
|  | 84 | 40.6 |
|  | 85 | 38.1 |
|  | 90 | 34.4 |
|  | 91 | 32.5 |
|  | 92 | 33.1 |
| (Maximum) | 84 | 38.8 |
| H-Y | 70 | 8.8 |
|  | 75 | 11.3 |
|  | 80 | 19.4 |
|  | 85 | 26.9 |
|  | 88 | 24.4 |
|  | 93 | 10.6 |
| (Maximum) | 86 | 26.6 |

Figure 3:
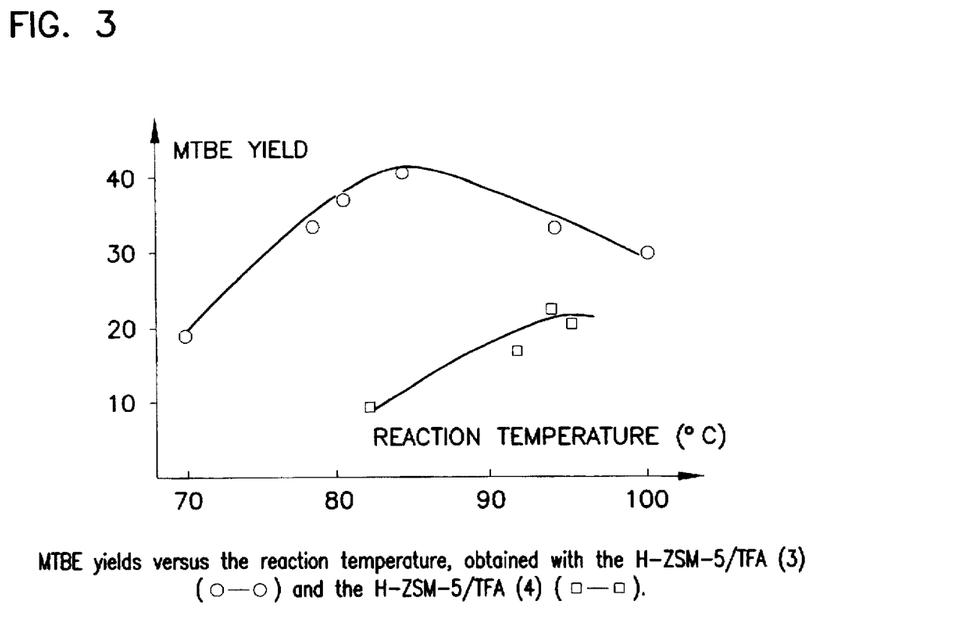
FIG. 3 illustrates the variation of MTBE yield with the temperature observed with H-ZSM-5/TFA (3%) and H-ZSM-5/TFA (4%).

FIG. 3 and Table 3 clearly demonstrate that though some increases in the MTBE was obtained by incorporating TFA onto the H-ZSM-5 zeolite, the resulting MTBE yield was still much lower than that of the Amberlyst 15.

Also, increasing the TFA loading to 4 wt % did not improve the production of MTBE, as shown in FIG. 3 and Table 3. On the contrary, a decrease in the MTBE yield indicates the existence of diffusional problems due to the TFA layer on the zeolite surface.

TABLE 3

Yield of MTBE versus reaction temperature (R = 1.0 and contact time = 2.5 h). (Maximum) are the maximum MTBE yields as derived from curves of FIG. 3 and 4.

| CATALYST | TEMPERATURE (°C.) | MTBE YIELD (C atom %) |
|---|---|---|
| H-ZSM-5/TFA (3) | 70 | 19.4 |
|  | 79 | 33.5 |
|  | 81 | 37.1 |
|  | 85 | 41.2 |
|  | 95 | 32.9 |
|  | 100 | 30.0 |
| (Maximum) | 85 | 41.2 |
| H-ZSM-5/TFA (4) | 82 | 9.1 |
|  | 91 | 16.5 |
|  | 94 | 21.8 |
|  | 96 | 20.0 |
| (Maximum) | 95 | 21.5 |
| H-Y/TFA (3) | 71 | 18.8 |
|  | 79 | 32.9 |
|  | 80 | 43.5 |
|  | 81 | 42.9 |
|  | 84 | 46.5 |
|  | 87 | 49.0 |
|  | 88 | 41.2 |
|  | 89 | 46.4 |
|  | 91 | 29.4 |
|  | 98 | 9.4 |
|  | 99 | 12.9 |
| (Maximum) | 85 | 47.9 |

Figure 4:
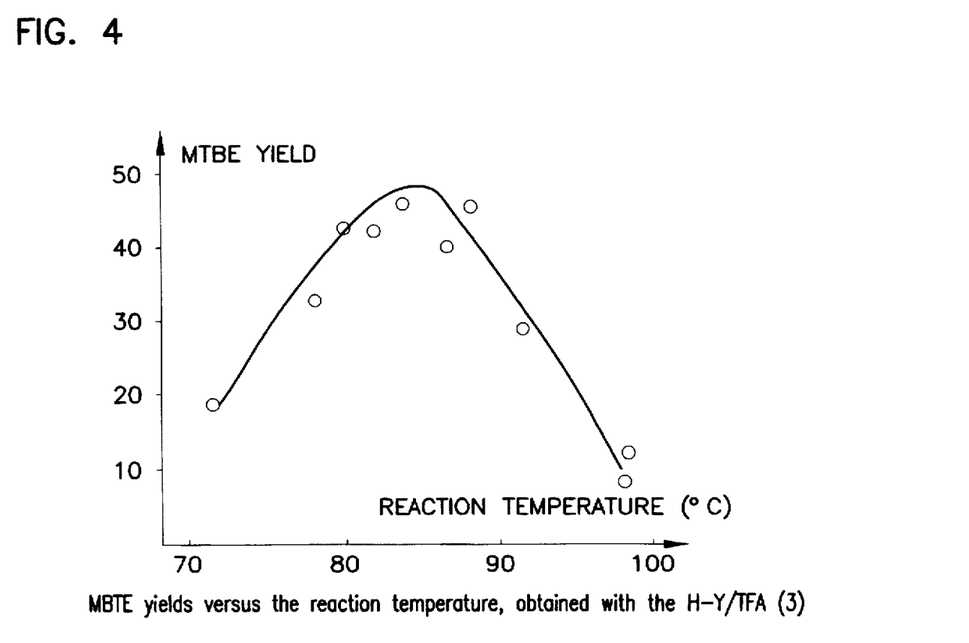
FIG. 4 illustrates the high yields of MTBE obtained with the H-Y/TFA (3%) of the present invention.

The level of MTBE obtained when H-Y/TFA (3%) used is as high as that of the Amberlyst 15 (Table 3 and FIG. 4)

Figure 5:
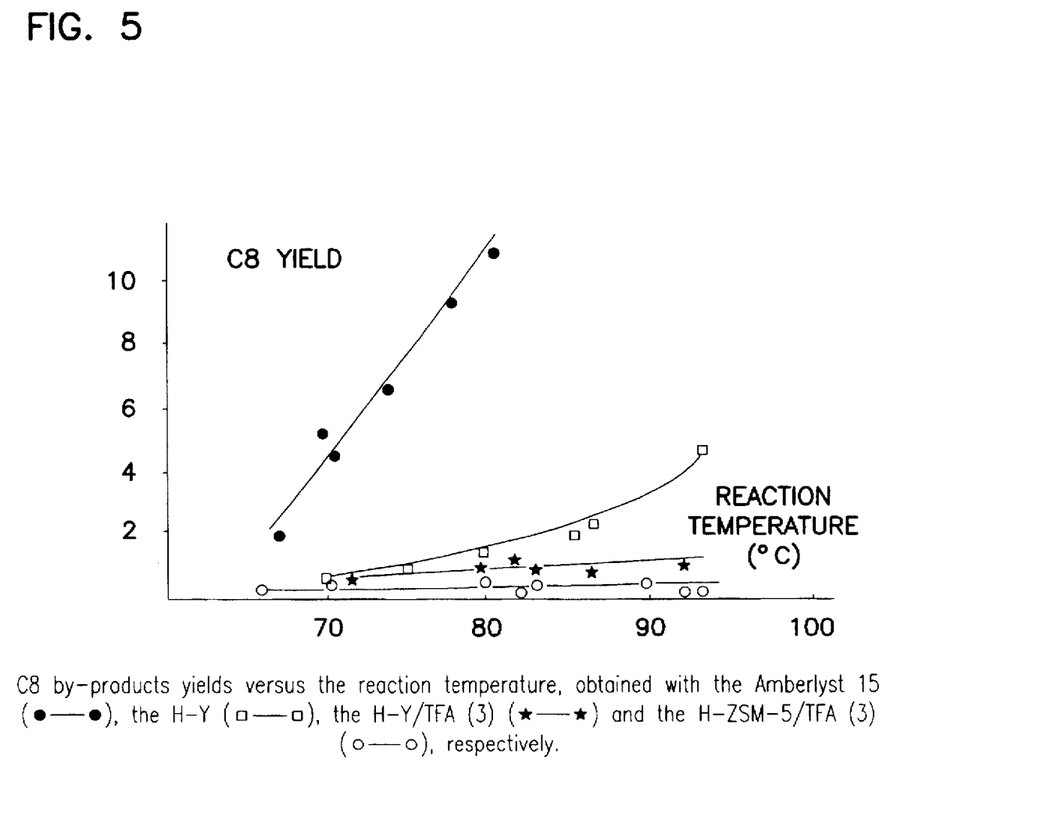
FIG. 5 illustrates the variation of $C_8$ by-products yield with the temperature observed with Amberlyst 15, H-Y/TFA (3%) of the present invention, H-Y, and H-ZSM-5/TFA (3%).

Finally, the production of the diisobutene by-products when H-Y/TFA (3%) is used, is much smaller than that of the Amberlyst 15 (FIG. 5 and Table 4). This is explained by the advantageous shape selectivity of the zeolite framework of the invention.

TABLE 4

Yield of $C_8$ (diisobutenes) by-products versus reaction temperature (R = 1.0 and contact time = 2.5 h). (Maximum) are the $C_8$ yields as derived from curves of FIG. 5, at temperatures which provide the maximum MTBE yields (TABLES 2 and 3).

| CATALYST | TEMPERATURE (°C.) | $C_8$ YIELD (C atom %) |
|---|---|---|
| Amberlyst 15 | 68 | 1.9 |
|  | 70 | 5.3 |
|  | 71 | 4.7 |
|  | 74 | 6.7 |
|  | 78 | 9.5 |
|  | 81 | 11.1 |
| (Maximum) | 70 | 4.6 |
| H-Y | 70 | 0.6 |
|  | 75 | 0.9 |
|  | 80 | 1.5 |
|  | 85 | 2.1 |
|  | 86 | 2.4 |
|  | 93 | 4.7 |
| (Maximum) | 86 | 2.5 |
| H-Y/TFA (3) | 71 | 0.6 |
|  | 80 | 0.9 |
|  | 82 | 1.2 |
|  | 83 | 0.9 |

TABLE 4-continued

Yield of $C_8$ (diisobutenes) by-products versus reaction temperature (R = 1.0 and contact time = 2.5 h). (Maximum) are the $C_8$ yields as derived from curves of FIG. 5, at temperatures which provide the maximum MTBE yields (TABLES 2 and 3).

| CATALYST | TEMPERATURE (°C.) | $C_8$ YIELD (C atom %) |
|---|---|---|
|  | 87 | 0.9 |
|  | 92 | 1.2 |
| (Maximum) | 85 | 0.9 |
| H-ZSM-5/TFA (3) | 65 | 0.2 |
|  | 70 | 0.3 |
|  | 80 | 0.4 |
|  | 82 | 0.2 |
|  | 83 | 0.4 |
|  | 90 | 0.5 |
|  | 92 | 0.3 |
|  | 93 | 0.3 |
| (Maximum) | 85 | 0.4 |

Figure 6:
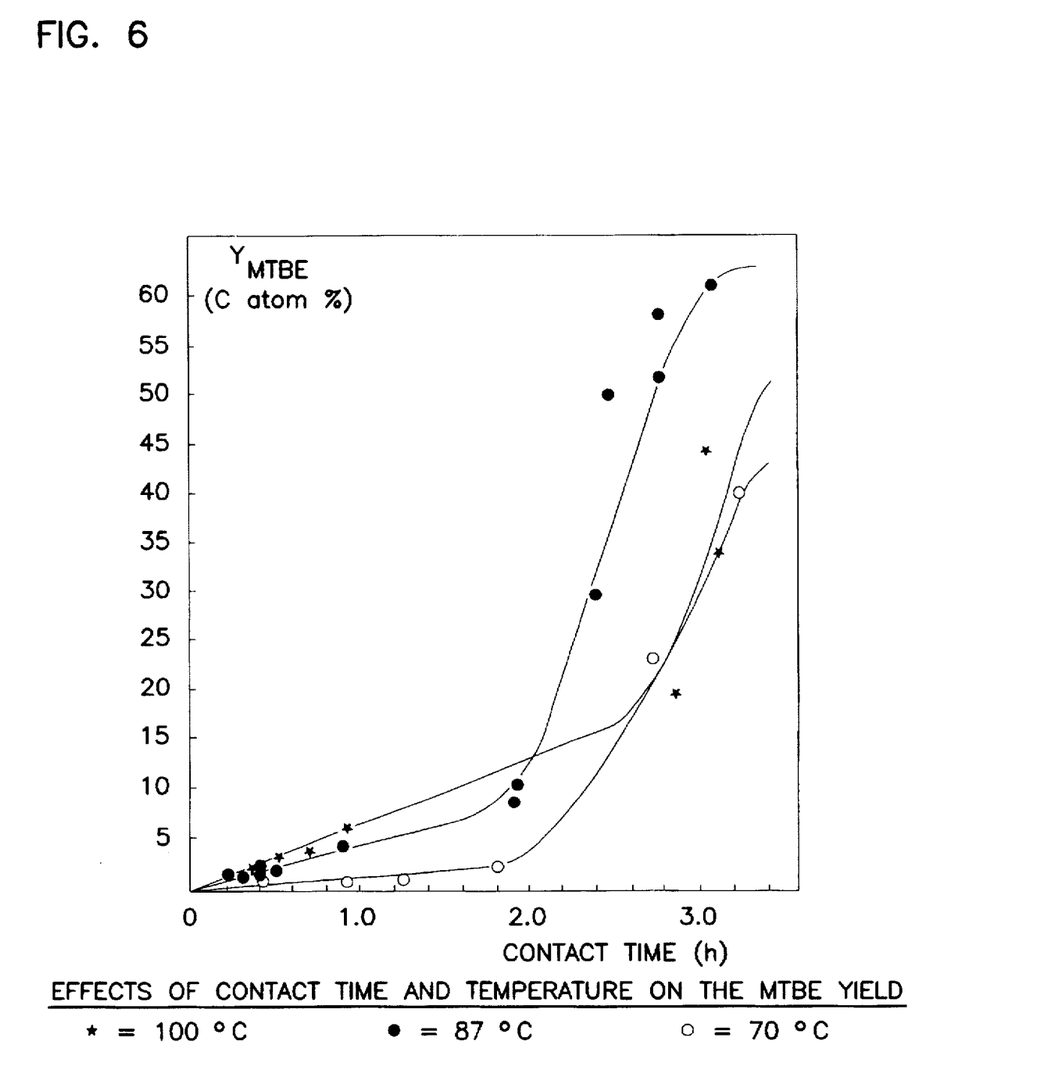
FIG. 6 illustrates the effects of the contact time and the reaction temperature on the yields of MTBE.

FIG. 6 and corresponding Table 5 illustrate the effects of the contact time and the reaction temperature on the yields of MTBE in the presence of the H-Y/TFA (3%) catalyst. Therefore, to achieve hight yield of MTBE, temperature of 85°–90° C. and contact time of at least 2.5 h, must be used.

TABLE 5

Influence of temperature and contact time on the yield of MTBE (Catalyst = H-Y/TFA (3); R = 1.5–2.0).

| TEMPERATURE (°C.) | CONTACT TIME (h) | MTBE YIELD (C atom %) |
|---|---|---|
| 70 | 0.42 | 0.9 |
|  | 0.90 | 1.4 |
|  | 1.24 | 1.4 |
|  | 1.80 | 2.5 |
|  | 2.70 | 22.9 |
|  | 3.24 | 39.3 |
| 87 | 0.20 | 1.8 |
|  | 0.30 | 1.4 |
|  | 0.40 | 1.8 |
|  | 0.45 | 2.5 |
|  | 0.90 | 4.3 |
|  | 1.90 | 8.9 |
|  | 1.93 | 10.7 |
|  | 2.40 | 29.3 |
|  | 2.45 | 48.9 |
|  | 2.62 | 50.7 |
|  | 2.65 | 56.8 |
|  | 3.05 | 59.6 |
| 100 | 0.37 | 2.1 |
|  | 0.55 | 3.2 |
|  | 0.70 | 3.9 |
|  | 0.92 | 5.1 |
|  | 2.85 | 19.3 |
|  | 3.00 | 43.2 |
|  | 3.05 | 33.2 |

Figure 7:
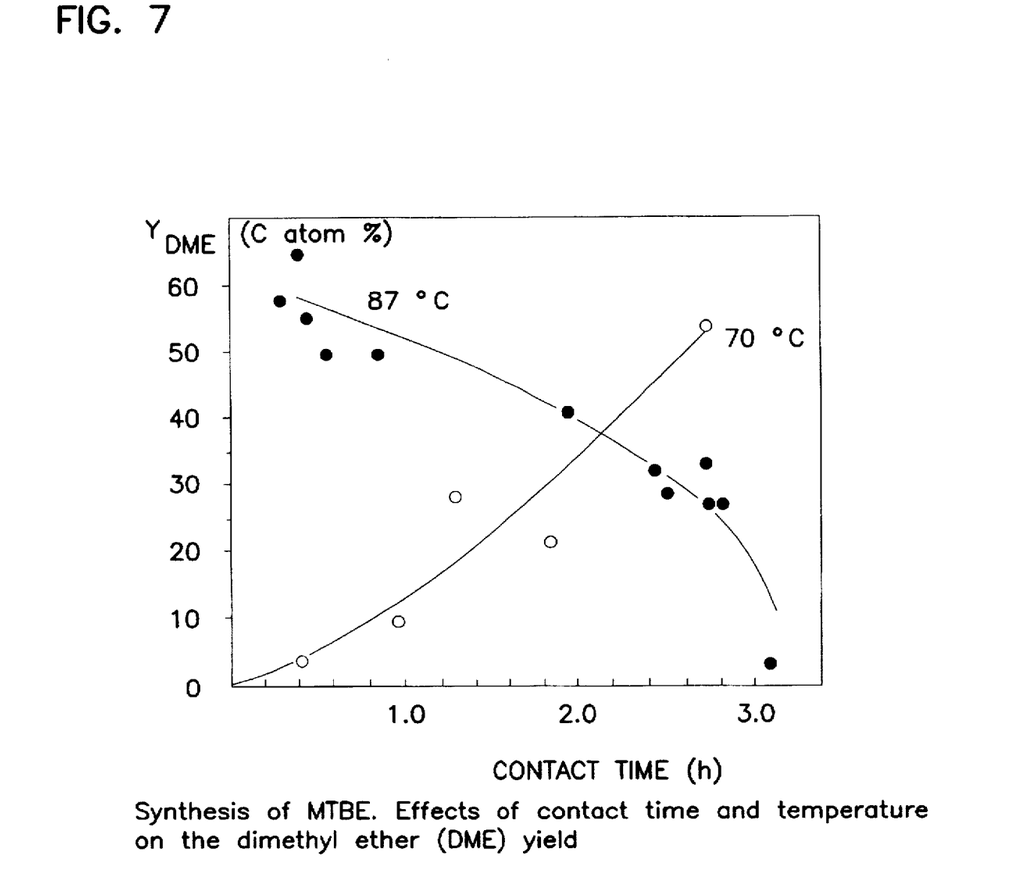
FIG. 7 illustrates the yield of ETBE by reaction of isobutene with ethanol over the H-Y/TFA (3) catalyst.

Table 6, which corresponds to FIG. 7, illustrates the yield of ETBE by reaction of isobutene with ethanol over H-Y/TFA (3%) catalyst of the present invention.

TABLE 6

Influence of temperature and contact time on the production of ETBE (Catalyst = H-Y/TFA (3); R (ethanol/isobutene = 1.5–2.0).

| TEMPERATURE (°C.) | CONTACT TIME (h) | ETBE YIELD (C atom %) |
|---|---|---|
| 91 | 0.52 | 1.5 |
|  | 0.80 | 8.7 |

TABLE 6-continued

Influence of temperature and contact time on the production of
ETBE (Catalyst = H-Y/TFA (3); R (ethanol/isobutene = 1.5–2.0).

| TEMPERATURE (°C.) | CONTACT TIME (h) | ETBE YIELD (C atom %) |
|---|---|---|
| | 1.00 | 13.2 |
| | 1.10 | 13.0 |
| | 1.15 | 13.6 |
| | 1.20 | 12.3 |
| | 1.25 | 11.5 |
| | 1.60 | 16.0 |
| | 1.90 | 18.7 |
| | 2.00 | 18.5 |
| | 2.70 | 25.3 |
| | 2.90 | 21.3 |
| | 3.10 | 33.6 |
| | 3.25 | 25.7 |
| | 3.28 | 22.4 |
| | 3.30 | 22.8 |
| | 3.40 | 21.5 |
| | 3.50 | 21.3 |
| | 3.80 | 20.4 |
| | 3.90 | 22.6 |
| 105 | 0.25 | 1.1 |
| | 0.60 | 2.3 |
| | 0.85 | 2.5 |
| | 1.10 | 7.0 |
| | 2.20 | 19.4 |
| | 2.75 | 20.4 |
| | 2.85 | 15.1 |
| | 2.95 | 12.6 |

In summary, the H-Y/TFA is as active as the Amberlyst 15 (Table 7). However, it is more shape selective, and more thermally and chemically resistant than the commercial ion-exchange resin catalyst.

TABLE 7

Catalytic results (MTBE systhesis in gaseous phase) obtained with the commercial Amberlyst 15 and the H-Y/TFA (3) catalyst of the present invention. (R = 1.0; contact time = 2.5 h).

| CATALYST | MAXIMUM MTBE YIELD (C Atom %) | TEMPERATURE (°C.) | $C_8$ BY-PRODUCTS PRODUCED AT MAXIMUM MTBE YIELD (C Atom %) |
|---|---|---|---|
| Amberlyst 15 | 48.8 | 70 | 4.6 |
| H-Y-TFA (3) | 47.9 | 85 | 0.9 |

What is claimed is:

1. A method of preparing methyl-t-butyl-ether (MTBE) from isobutene and methanol, said method comprising the steps of:

reacting said isobutene and methanol at a temperature of about 80° C. to about 100° C. at a pressure of at least about 200 psig. in the presence of a catalyst comprising an acid-form Y-zeolite catalyst base having incorporated thereon about 0.5 to 7 wt % of trifluoromethanesulfonic acid.

2. A method according to claim 1 wherein said catalyst comprises about 5 to 50 wt-% of an inert binder.

3. A method according to claim 2 wherein said inert builder comprises bentonite.

4. A method according to claim 1 wherein catalyst comprises a Y-zeolite catalyst base having a pore size of at least 7.4 Angstroms.

5. A method according to claim 1 wherein said catalyst base has incorporated thereon about 3 to 5 wt % of trifluoromethanesulfonic acid.

6. A method according to claim 1 wherein said catalyst base has incorporated thereon about 3 wt % of trifluoromethanesulfonic acid.

7. A method for the preparation of methyl-t-butyl-ether (MTBE) or ethyl-t-butyl-ether (EBTE) which comprises the steps of reacting isobutene with alcohol selected from the group consisting of methanol and ethanol at a temperature of about 80° C. to about 100° C. at a pressure of at least about 200 psig. in the presence of the catalyst which comprises from about 0.5% to about 7% by weight of trifluoromethanesulfonic acid incorporated onto an acid-form Y-zeolite.

8. A method according to claim 7 wherein said catalyst comprises about 5 to 50 wt % of an inert binder.

9. A method of claim 8, wherein said inert builder comprises bentonite.

10. A method of claim 7, wherein said catalyst comprises Y-zeolite catalyst base having a pore size of at least 7.4 Angstroms.

11. A method according to claim 7 wherein said catalyst base has incorporated thereon about 3 to 5 wt % of trifluoromethanesulfonic acid.

12. A method of preparing ethyl-t-butyl-ether (ETBE) from isobutene and ethanol, said method comprising the steps of reacting said isobutene and ethanol at a temperature of about 80° C. to about 100° C. at a pressure of at least about 200 psig. in the presence of a catalyst comprising an acid-form Y-zeolite catalyst base having incorporated thereon about 0.5 to 7 wt % of trifluoromethanesulfonic acid.

13. A method according to claim 12 wherein said catalyst comprises about 5 to 50 wt % of an inert binder.

14. A method according to claim 13 wherein said inert binder comprises bentonite.

15. A method according to claim 12 wherein said catalyst comprises a Y-zeolite catalyst base having a pore size of at least 7.4 Angstroms.

16. A method according to claim 12 wherein said catalyst base has incorporated thereon about 3 to 5 wt % of trifluoromethanesulfonic acid.

17. A method according to claim 12 wherein said catalyst base has incorporated thereon about 3 wt % of trifluoromethanesulfonic acid.

* * * * *

UNITED STATES PATENT AND TRADEMARK OFFICE
CERTIFICATE OF CORRECTION

PATENT NO. : 5,780,689
DATED : JULY 14, 1998
INVENTOR(S) : MAO

It is certified that error appears in the above-identified patent and that said Letters Patent is hereby corrected as shown below:

Col. 2, line 23: insert --activity and product selectivity in the ethanol dehydration and acetone conversion-- between the words "catalytic" and "to"

Col. 6, line 48: "28.6" should read --28.8--

Signed and Sealed this

Thirteenth Day of June, 2000

*Attest:*

Q. TODD DICKINSON

*Attesting Officer*          *Director of Patents and Trademarks*